United States Patent
Gifford et al.

(10) Patent No.: US 6,914,427 B2
(45) Date of Patent: Jul. 5, 2005

(54) EDDY CURRENT PROBE HAVING SENSING ELEMENTS DEFINED BY FIRST AND SECOND ELONGATED COILS AND AN ASSOCIATED INSPECTION METHOD

(75) Inventors: Carl B. Gifford, Buckley, WA (US); Clyde T. Uyehara, Kent, WA (US)

(73) Assignee: The Boeing Company, Seattle, WA (US)

(*) Notice: Subject to any disclaimer, the term of this patent is extended or adjusted under 35 U.S.C. 154(b) by 0 days.

(21) Appl. No.: 10/389,420

(22) Filed: Mar. 14, 2003

(65) Prior Publication Data

US 2004/0178790 A1 Sep. 16, 2004

(51) Int. Cl.$^7$ .................. G01N 27/82; G01R 33/12
(52) U.S. Cl. .................. 324/242; 324/243; 324/240
(58) Field of Search ................ 324/219, 220, 324/228–243

(56) References Cited

U.S. PATENT DOCUMENTS

| | | | |
|---|---|---|---|
| 4,029,899 A | * 6/1977 | Gordon | 341/5 |
| 4,283,714 A | 8/1981 | Trenkler et al. | |
| 4,380,768 A | * 4/1983 | Palombo et al. | 346/74.5 |
| 4,706,021 A | 11/1987 | Chamuel | |
| 4,799,010 A | 1/1989 | Muller | |
| 5,047,719 A | 9/1991 | Johnson et al. | |
| 5,082,286 A | * 1/1992 | Ryan et al. | 273/238 |
| 5,182,513 A | 1/1993 | Young et al. | |
| 5,399,968 A | * 3/1995 | Sheppard et al. | 324/242 |
| 5,420,379 A | * 5/1995 | Zank et al. | 178/19.03 |
| 5,611,534 A | * 3/1997 | Takemoto et al. | 273/121 B |
| 5,793,206 A | 8/1998 | Goldfine et al. | |
| 5,913,820 A | * 6/1999 | Bladen et al. | 600/407 |
| 6,344,739 B1 | * 2/2002 | Hardy et al. | 324/220 |
| 6,420,867 B1 | 7/2002 | Goldfine et al. | |
| 6,433,542 B2 | 8/2002 | Goldfine et al. | |
| 6,593,884 B1 | * 7/2003 | Gilboa et al. | 342/448 |
| 2002/0163333 A1 | 11/2002 | Schlicker et al. | |

FOREIGN PATENT DOCUMENTS

| | | | |
|---|---|---|---|
| CH | 673896 | * | 4/1990 |
| EP | 0 381 848 A | | 8/1990 |
| EP | 0381848 | * | 8/1990 |
| EP | 0 512 796 A | | 11/1992 |
| JP | 8-280820 | * | 10/1996 |
| JP | 11-51905 | * | 2/1999 |
| JP | 11 051905 A | | 2/1999 |
| SU | 1 462 178 A | | 2/1989 |

* cited by examiner

*Primary Examiner*—Jay Patidar
(74) *Attorney, Agent, or Firm*—Alston & Bird LLP

(57) ABSTRACT

An eddy current probe and associated method of inspecting a structure are provided that are capable of generating a two-dimensional image of the structure, generally in real time. The eddy current probe includes an eddy current probe array having a plurality of first and second coils that cross one another to define a plurality of sensing elements. The eddy current probe array may also include a plurality of magnetically permeable core elements located coincident with respective sensing elements and at least partially encircled by respective first and second coils. The eddy current probe may also include an alternating current source electrically connected to the first coils and sense electronics for sensing current induced in the second coils. In operation, the current sensed in the second coils represents at least one characteristic of the structure, such as the electrical conductivity of the structure.

20 Claims, 3 Drawing Sheets

EDDY CURRENT PROBE HAVING SENSING ELEMENTS DEFINED BY FIRST AND SECOND ELONGATED COILS AND AN ASSOCIATED INSPECTION METHOD

FIELD OF THE INVENTION

The present invention relates generally to eddy current probes and associated inspection methods and, more particularly, to eddy current probes having a two-dimensional array of sensing elements defined by a plurality of coils that may extend perpendicularly relative to one another.

BACKGROUND OF THE INVENTION

One common type of non-destructive inspection (NDI) or non-destructive test (NDT) is an eddy current inspection. During this inspection process, eddy current sensors impart and detect eddy currents within a structure, particularly in metallic and other conductive structures. The data acquired by an eddy current sensor may be processed and displayed so as to identify cracks within and/or corrosion upon the structure. While eddy current inspection is advantageous for detecting cracks, eddy current inspection may be utilized in other applications known to those skilled in the art such as dent profile mapping, lightning strike evaluation, fire damage evaluation and the like.

Both automated and manual eddy current inspection systems have been developed. In automated inspection systems, one or more eddy current sensors are moved in a controlled fashion along the structure that is being inspected. The data collected by the eddy current sensor(s) is processed and associated with the location on the structure from where the data was obtained. While automated eddy current inspection systems provide for relatively fast and accurate inspections, the automated systems are quite expensive. In many cases, structures must be inspected in the field since, for example, it may not be feasible or it may be too expensive and/or time-consuming to transport the structure to an offsite laboratory for inspection. In these instances, the automated eddy current inspection systems may prove to be too bulky for routine field inspections. Additionally, the use of an automated eddy current inspection system in the field may further be hampered by the inability of an automated system to be powered by a local power supply, such as batteries, and the automated eddy current inspection system may, instead, need to be connected to a remote power supply via bulky power cables.

As such, eddy current sensors that may be manually scanned by a technician, such as during the routine field inspection of the structure, are available. Typically, a trained technician holds the sensor and moves the sensor along the structure such that the eddy current sensor inspects all desired portions of the structure. A typical eddy current probe includes a single sensing element, although some eddy current probes include a linear array of coils. Current may be induced in the coil(s) based upon an input drive signal, typically consisting of an alternating current (AC) input provided by the eddy current sensor, and the current induced in that portion of the structure proximate the coil(s) as a result of the AC input signal. Based upon the current induced within each coil, at least one characteristic, such as the electrical conductivity, of those portions of the structure proximate the respective coils may be determined.

Conventional eddy current sensors adapted for manual inspection of a structure also generally include a position encoder. The position encoder is initialized with the eddy current sensor disposed at a predetermined reference position relative to the structure. The output of the position encoder can therefore be analyzed to determine the current position of the eddy current sensor relative to the structure. Thus, the measurements of the current induced within each coil may be associated with a corresponding location upon the surface of the structure. Thus, a spatial map of at least one characteristic of the structure may be constructed from which cracks, corrosion or the like may be identified.

Utilizing conventional eddy current sensors during the manual inspection of a structure, a two-dimensional image of the structure and, in particular, of at least one characteristic of the structure could only be constructed once the sensor had been moved along the surface of the structure with the current induced in each coil of the measured at each position of the eddy current sensor. Thus, a two-dimensional image of the structure cannot be created in real time. Moreover, for the measurement of the current induced in each coil of the eddy current sensor to be meaningful and for the resulting two-dimensional image to be accurate, the position of the eddy current sensor must be accurately provided by the position encoder. Thus, any slippage between the position encoder and the underlying structure would render any subsequently obtained measurements of the current induced in the coil(s) inaccurate since the relative position upon the surface of the structure at which those measurements were obtained cannot be accurately defined. Moreover, since the generation of the two-dimensional image relies upon the movement of the sensor in one direction, the movement of the eddy current sensor in any other direction would also prevent a two-dimensional image of the structure from being properly created. As such, the quality of the inspection is dependent, in large part, upon the performance of the technician in moving the eddy current sensor along the surface of the structure. Thus, the manual scanning of structures with a conventional eddy current sensor is time-consuming, labor-intensive and prone to human error. Additionally, manual scanning of an eddy current sensor over the surface of a structure may fatigue the technician.

As such, it would be desirable to develop an improved eddy current probe and associated inspection method that permits a structure to be scanned more quickly, while permitting the eddy current probe to be moved in any desired direction along the surface of the structure. In addition, it would be desirable to provide an improved eddy current probe and associated inspection method that is capable of producing a real time display of at least one characteristic of the structure under inspection.

BRIEF SUMMARY OF THE INVENTION

An improved eddy current probe and associated method of inspecting an object are provided by the present invention. The eddy current probe of the present invention is capable of generating a two-dimensional image of at least a portion of a structure under inspection such that cracks, corrosion, dents or damage attributable to lightning strikes, fire or the like, may be readily determined. The eddy current probe and associated inspection method of one embodiment may generate the two-dimensional image in real time, thereby eliminating the requirement of tracking the position of the probe relative to the surface of the structure under inspection as required by conventional manual eddy current probes. Thus, the eddy current probe of the present invention may be moved more freely over a structure than conventional manual eddy current inspection systems. Additionally, the generation of a two-dimensional image of the structure under inspection in real time by the eddy current probe and the inspection method of one embodiment of the present invention permits the structure to be inspected more rapidly than conventional systems, thereby reducing any fatigue otherwise experienced by a technician.

An eddy current probe, according to one embodiment, includes a plurality of first coils oriented in a first direction. For example, the coils may be elongated with the major axis of each first coil extending in the first direction. The eddy current probe also includes a plurality of second coils oriented in a second direction. As with the first coils, the plurality of second coils may be elongated so as to define a major axis that extends in the second direction. The second direction is different than the first direction such that the plurality of second coils cross the plurality of first coils to define respective sensing elements. Although the first and second coils may be oriented in various fashions, the first and second coils of one embodiment are perpendicular to one another. Regardless of the orientation, the plurality of first and second coils generally define an eddy current probe array.

The eddy current probe array may also include a plurality of magnetically permeable core elements at least partially encircled by respective pairs of the first and second coils. In one embodiment, the core elements include a plurality of medial core elements and a plurality of peripheral core elements disposed about the medial core elements. In this regard, the plurality of core elements may be disposed in a two-dimensional array having a plurality of linear arrangements of the core elements. At least one linear arrangement may include a plurality of medial core elements disposed between a pair of peripheral core elements. As such, either a first coil or a second coil may be wrapped about the pair of peripheral core elements so as to also encircle the plurality of medial core elements disposed therebetween.

The eddy current probe may also include an alternating current source electrically connected to respective ones of the first coils and sense electronics for sensing current induced in respective ones of the second coils. In operation, the current sensed in a respective second coil is therefore representative of at least one characteristic of the structure proximate the corresponding sensing element defined by the crossing of the respective second coil and the first coil to which current is supplied. For example, the current sensed by the respective second coil may be representative of the conductivity of the structure proximate the corresponding sensing element which, in turn, can be indicative of and utilized to detect cracks, corrosion and the like.

In one advantageous embodiment, the alternating current source sequentially supplies current to each of the first coils. Additionally, the current induced in each of the second coils may be sequentially sensed while the alternating current is provided to a respective first coil. As such, alternating current may be applied to one of the first coils and the current induced in each of the second coils may be sequentially sensed. Thereafter, current may be applied to another one of the first coils and the current induced in each of the second coils may again be sequentially sensed. This process may be continued until current has been supplied to each of the first coils. During the process, the eddy current probe array may be moved so as to inspect another portion of the object.

In order to sequentially connect the alternating current source to each of the first coils, the eddy current probe may also include a multiplexer. Similarly, the sense electronics may include a multiplexer for sequentially connecting to each of the second coils in order to sense the current induced therein. The sense electronics may also include a processing element for associating the current induced within a respective second coil with the respective sensing element defined by the intersection of the first coil to which the alternating current source is electrically connected and the respective second coil. Further, the eddy current probe may include a display for depicting at least one characteristic of the structure under inspection based upon the current induced in respective ones of the second coils and the associated sensing element. In one advantageous embodiment, the display may depict at least one characteristic of the structure in real time such that the relative position of the eddy current probe array with respect to the structure under inspection need not be monitored by a position encoder or the like since the technician can view the display of the structure under inspection in real time to determine if the portion of the structure currently being inspected has a crack, corrosion or the like.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
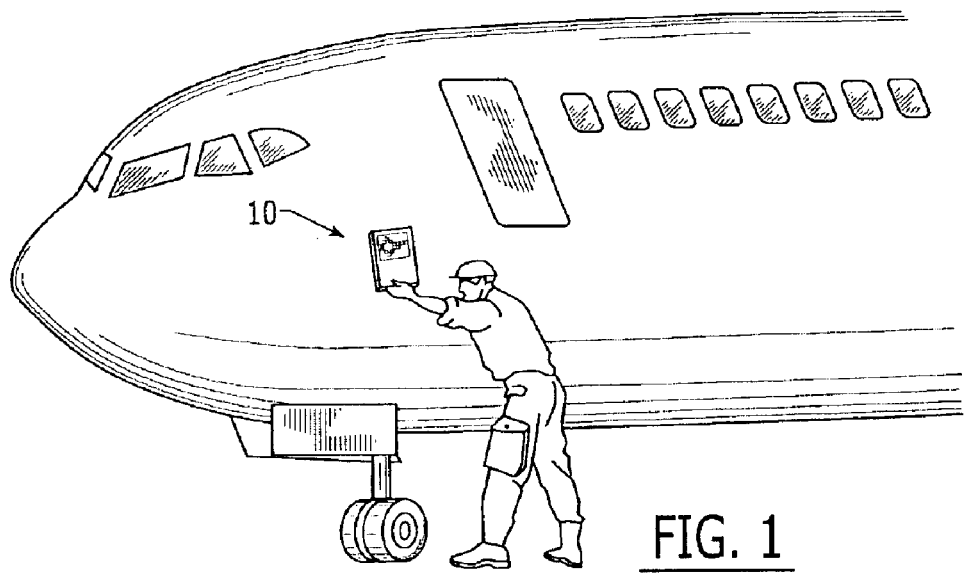
FIG. 1 is a perspective view of a technician inspecting a structure, such as a portion of an aircraft, with an eddy current probe according to one embodiment of the present invention.

As shown by way of example in FIG. 1, an eddy current probe 10 is provided according to the present invention for conducting eddy current inspections of various objects. While FIG. 1 depicts the inspection of a portion of the surface of an aircraft, the eddy current probe and the associated inspection method of the present invention may be utilized to inspect a wide variety of other objects including other types of vehicles, bridges, buildings and other structures that are at least partially electrically conductive. As also shown in FIG. 1, the eddy current probe and associated inspection method of the present invention are particularly advantageous for the manual inspection of a structure in the field. However, the eddy current probe and associated inspection method may be utilized in conjunction with an automated inspection process and/or may be utilized in a laboratory environment, if so desired.

As described below, the eddy current probe 10 may be configured to provide eddy current inspections at various depths within the structure including deep eddy current inspections, shallow eddy current inspections, and surface inspections. Regardless of the type of structure being inspected, the environment in which the structure is inspected, and the type of eddy current inspection being conducted, the eddy current probe and the associated inspection method of the present invention permit a technician to inspect an object more rapidly than conventional manual eddy current inspection techniques and provide the technician with much greater flexibility in the movement of the eddy current probe over the surface of the structure since real time displays of the structure under inspection may be provided, thereby eliminating the requirement of conventional manual inspection systems that the position of the eddy current probe with respect to the surface of the structure under inspection must be tracked by a position encoder or the like.

Figure 2:
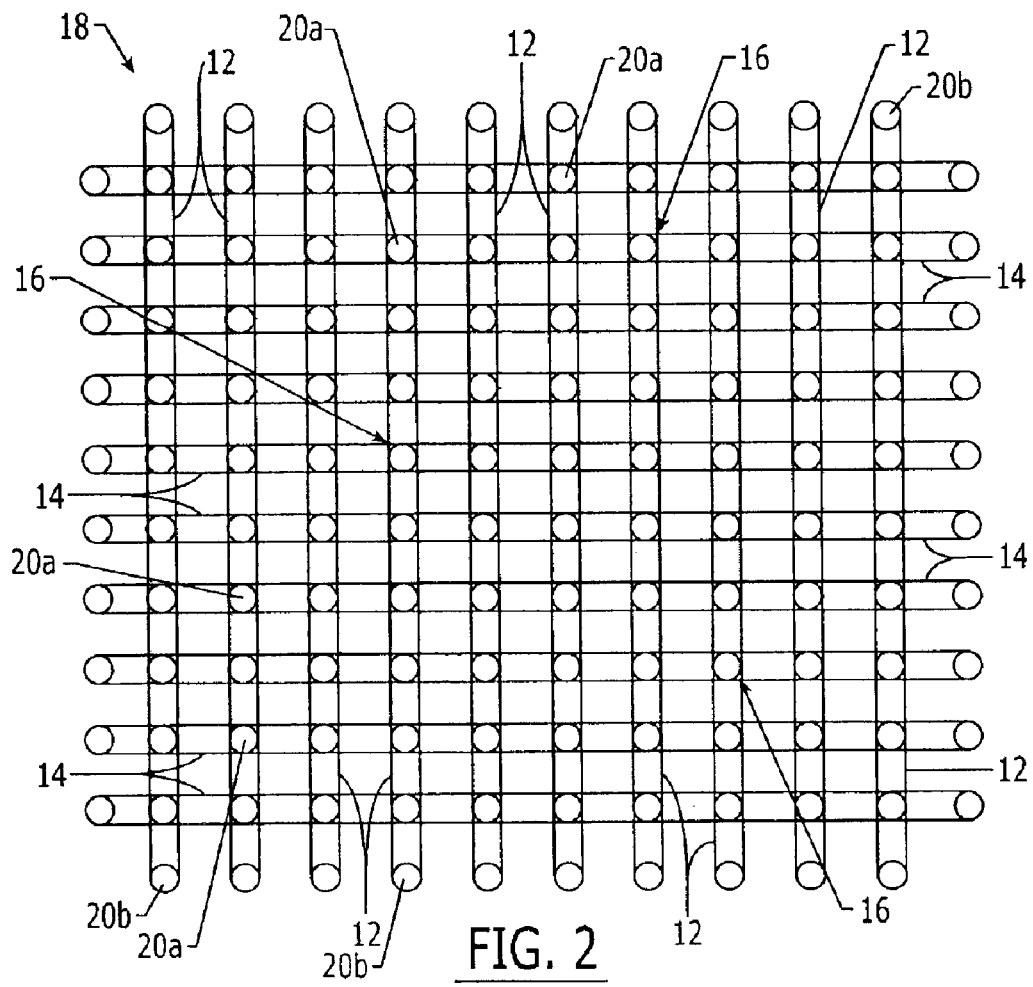
FIG. 2 is a schematic representation of an eddy current probe array of an eddy current probe according to one embodiment of the present invention.
Figure 2A:
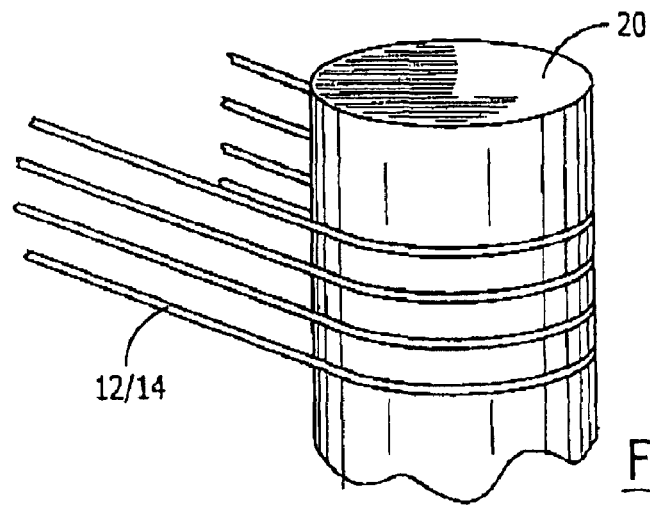
FIG. 2A is a perspective view of a core element encircled by a plurality of turns of a conductive member.

As shown in FIG. 2, the eddy current probe 10 includes a plurality of first coils 12 oriented in a first direction and a plurality of second coils 14 oriented in a second direction. In this regard, each first coil and each second coil is generally elongated. As such, each first coil typically defines a major axis extending in the first direction, while each second coil defines a major axis extending in the second direction. The second direction is different than the first direction and, in one advantageous embodiment, is perpendicular to the first direction such that the plurality of second coils cross the plurality of first coils to define respective sensing elements 16 at the points of intersection, several of which are identified in FIG. 2. As shown in FIG. 2A, each coil may be comprised of one or more turns of wire with the number of turns of wire generally being dictated by the application. For example, eddy current probes utilized for deep eddy current inspection generally have coils comprised of a relatively large number of turns, such as 1000 turns or more, so as to produce strong, penetrating magnetic fields at relatively low frequencies. For shallower eddy current inspections, including surface inspections, a coil of wire having relatively low impedance and generally consisting of only a few turns, such as 32 turns in one example, is required. The first and second coils may be formed of various electrically conductive members but, in one advantageous embodiment, are formed of magnet wire having a core of copper coated with an insulative material, such as enamel. Since the coils are generally formed by an insulated wire, the first and second coils may physically contact one another at those locations at which the first and second coils cross one another. As a result of the insulative coating on the wire that forms the first and second coils, however, the first and second coils are not in direct electrical contact.

The plurality of first and second coils 12, 14 generally define an eddy current probe array 18. While the first and second coils may be oriented in different fashions relative to one another, the eddy current probe array of one embodiment is a rectangular array as shown in FIG. 2. While different numbers of first and second coils may be utilized, the eddy current probe array of one embodiment includes equal numbers of first and second coils, such as 10, 16 or more first coils and a like number of second coils so as to define a square eddy current probe array. Additionally, the spacing between each of the first coils and each of the second coils may be defined in various manners. In one embodiment, however, each first coil is spaced apart from other adjacent first coils by the same distance, such as 1.0 inch, 0.100 inch, 0.040 inch, 0.020 inch or another spacing depending upon the desired resolution. In this embodiment, each of the second coils is generally spaced apart from adjacent second coils by the same distance. As will be apparent to those skilled in the art, the spacing between the first and second coils generally defines the resolution of the eddy current probe 10, while the combination of the spacing between the first and second coils and a number of first and second coils that comprise the eddy current probe array define the size of the eddy current probe array and, in turn, the size of the portion of the structure that is inspected at any one time.

In order to enhance the electromagnetic coupling between the eddy current probe array 18 and the structure under inspection, the eddy current probe array may also include a plurality of magnetically permeable core elements 20. As shown in FIG. 2, the core elements may be at least partially encircled by respective pairs of the first and second coils 12, 14. As shown, the eddy current probe array may include a core element coincident with each sensing element 16. In other words, the eddy current probe array may include a respective core element at each location at which a first coil crosses a second coil. Alternatively, the eddy current probe array may include a lesser number of core elements, if so desired. Typically, the core elements may have various shapes, such as cylindrical or rectangular, and may be elongate or rod-like to thereby define an axis that extends perpendicular to the respective planes defined by the first and second coils. The core elements may have various sizes with smaller core elements permitting the first and second coils to be packed tighter in order to increase the resolution of the eddy current probe. However, smaller core elements generally are more fragile and harder to machine. Additionally, smaller core elements tend to produce shallower magnetic fields which is advantageous for surface inspections, but not for subsurface eddy current inspection in which deeply penetrating magnetic fields are desirable.

In one embodiment, each core element 20 has a rectangular solid shape with a square cross section that is 0.020 inch on each side and a length of 0.100 inch. In this embodiment, a gap of 0.020 inches is provided between adjacent core elements with the size of the gap between adjacent core elements generally depending upon the space required for the first and second coils of wire 12, 14 which, in turn, typically depends upon the number of turns and the diameter of the wire. While the foregoing exemplary embodiment is advantageous for eddy current surface inspections, eddy current probes designed for subsurface inspections generally require larger core elements with greater spacing therebetween to permit larger coils of wire to be wrapped about the core elements. By way of another example, core elements that have a rectangular solid shape and a square cross section may be fabricated that measure 0.500 inch per side and that are 1.00 inch in length, thereby sacrificing spatial resolution but increasing the depth within the structure at which the eddy current inspection is conducted.

The core elements 20 may be formed of any of a number of magnetically permeable materials so as to enhance the magnetic field generated by current passing through the first coils 12 as described below. For example, the core elements may be comprised of ferrite or ferromagnetic steel. Although not shown in FIG. 2, the core elements may be mounted to or otherwise extend from a substrate or base member so as to maintain the core elements and, in turn, the first and second coils in proper relative position. The substrate or base member may be formed of various materials, such as a printed circuit board or the like. Alternatively, a piece of ferromagnetic steel may define both the core elements and the substrate or base member. For example, grooves may be cut in both the first and second directions in the piece of ferromagnetic steel. Since the grooves do not cut entirely through the piece of ferromagnetic steel, the core elements that are defined by the plurality of grooves are not completely independent, but continue to be integrally joined through the uncut portion of the piece of ferromagnetic steel to the other core elements.

The substrate and, in turn, the core elements 20 may be planer which is advantageous for the eddy current inspection of flat or nearly flat structures. In some applications, however, the eddy current probe 10 is designed to inspect structures having a non-flat contour, such as a curved structure. In this regard, the core elements may be arranged in a shape that approximates the contour of the structure. For example, the substrate that carries the core element may be formed to have a desired shape or contour to thereby facilitate eddy current inspection of contoured structures.

In one embodiment, the core elements 20 are only disposed coincident with respective sensing elements 16 of the eddy current probe array 18. In another embodiment depicted in FIG. 2, however, the core elements include both a plurality of medial core elements 20a disposed coincident with the respective sensing elements and a plurality of peripheral core elements 20b disposed about the medial core elements. In this embodiment, the core elements may be disposed in a two-dimensional array having a plurality of linear arrangements of the core elements. At least one and, more typically, each linear arrangement includes a plurality of medial core elements disposed between a pair of peripheral core elements. Thus, a respective coil, such as either a first coil 12 or a second coil 14, may be wrapped about the pair of peripheral core elements, thereby also encircling the plurality of medial core elements disposed therebetween. By utilizing peripheral core elements about which to wrap the respective coil, the eddy current probe array may provide more uniform measurements since the medial core elements located coincident with respective sensing elements will be at least partially encircled by a respective first coil and a respective second coil to the same degree, that is, the respective first coil will pass on opposite sides of the core element, while the corresponding second coil will also pass the core element on opposite sides, albeit different sides than the respective first coil.

Figure 3:
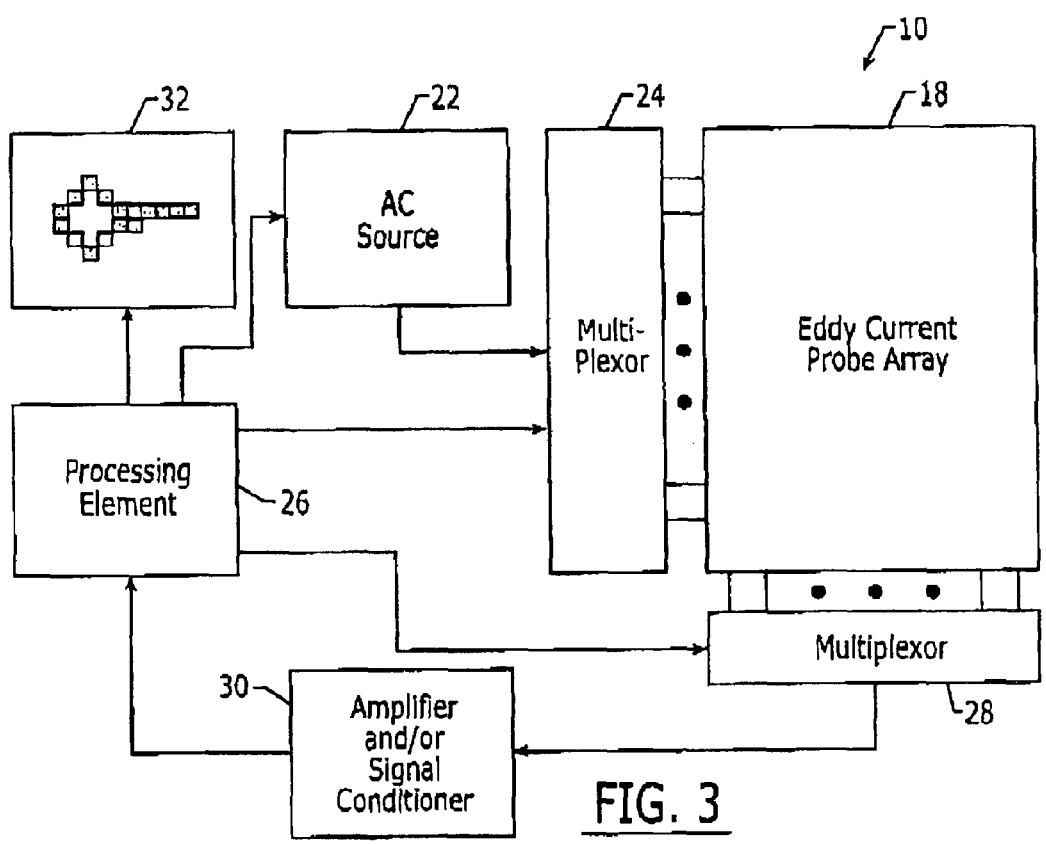
FIG. 3 is a block diagram of an eddy current probe according to one embodiment of the present invention.

In addition to the eddy current probe array 18, the eddy current probe 10 of the present invention includes an alternating current (AC) source 22 electrically connected to respective ones of the plurality of first coils 12. As shown in FIG. 3, the AC source is preferably electrically connected to the eddy current probe array so as to be sequentially connected to each of the first coils. In this regard, the eddy current probe may also include a multiplexer 24, typically operating under control of a processing element 26 as described below, for sequentially connecting the AC source to each of the first coils in turn.

The eddy current probe 10 also includes sense electronics for sensing current induced in respective ones of the plurality of second coils 14. In this regard, the sense electronics preferably sequentially senses the current induced in each of the second coils while the AC source 22 provides current to a respective first coil 12. As such, the sense electronics may also include a multiplexer 28, typically operating under control of the processing element 26 as described below, for sequentially connecting to each of the second coils in order to sense the current induced therein. Alternatively, the sense electronics may simultaneously sense the current in some or all of the second coils while the AC source provides current to a respective first coil.

The sense electronics may also include an amplifier and/or signal conditioning electronics 30 to appropriately condition the signals induced in the second coils 14. As will be apparent to those skilled in the art, the current induced in the second coils is indicative of the complex impedance of that portion of the structure proximate the respective sensing element 16 and, as such, has a resistive component and an inductive reactance component. Thus, the signal conditioning electronics may be utilized to impart a phase change to the received signals, thereby emphasizing or, alternatively, suppressing a respective component of the complex impedance. While the simultaneous sensing of the current induced in multiple second coils may increase the speed with which the induced currents can be measured as mentioned above, this simultaneous sensing may require a plurality of sets of amplifiers and/or signal conditioning electronics, one of which is associated with each of the second coils.

Figure 4:
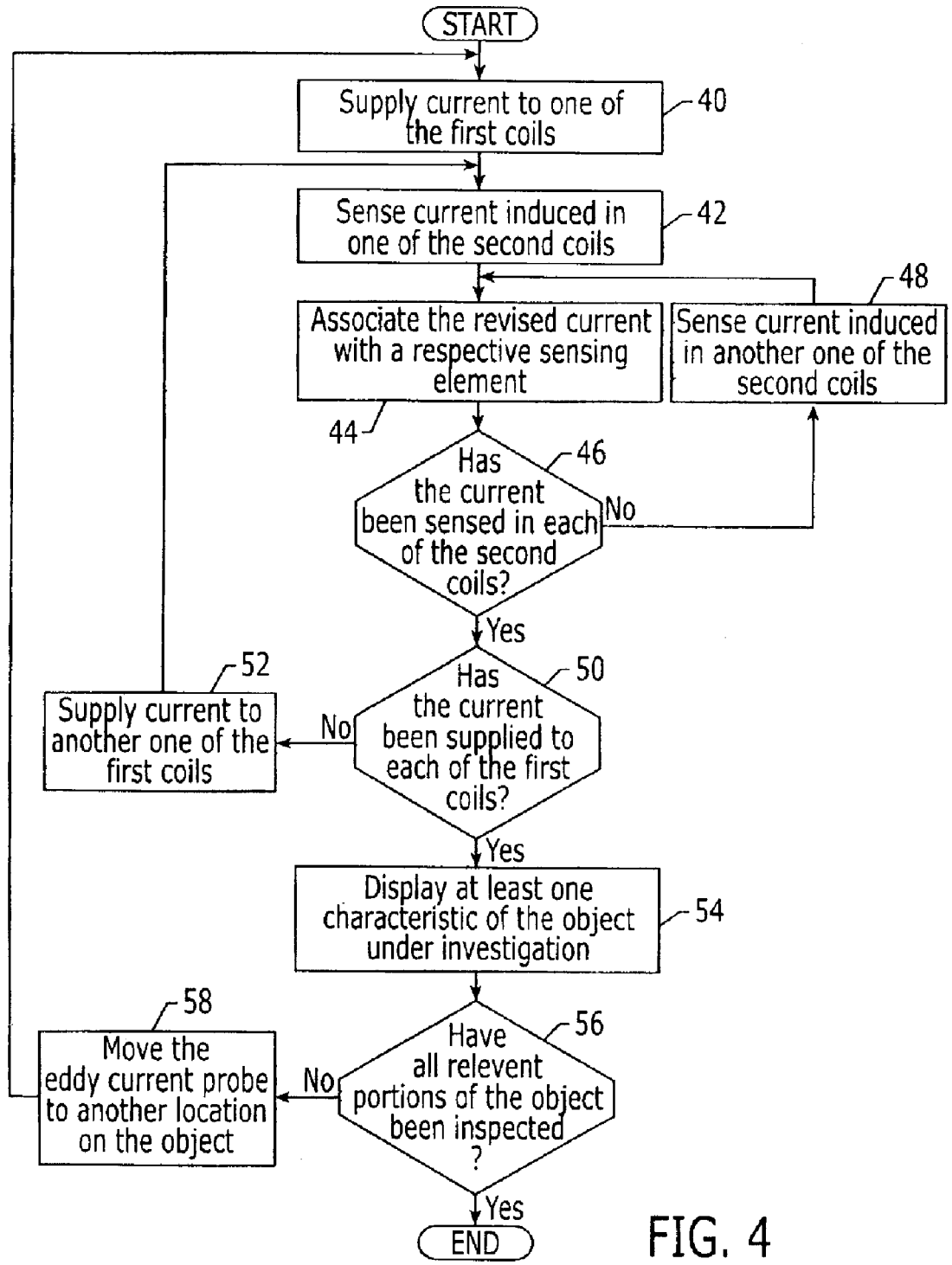
FIG. 4 is a flow chart illustrating operations performed in accordance with the method of conducting an eddy current inspection according to one embodiment of the present invention.

As shown in FIG. 3, the eddy current probe 10 also generally includes a processing element 26, such as a microprocessor, a computer, such as a personal computer, or other high level processor. The processing element preferably controls the AC source 22 and the associated multiplexer 24, as well as the sense electronics during the eddy current inspection of a structure. As depicted in FIG. 4, the processing element may direct the AC source and the associated multiplexer to supply current to a respective first coil 12. See step 40. As known to those skilled in the art, the magnetic field created by the AC current flowing through the first coil may induce a current in the structure under inspection. The resulting magnetic field generated by the AC current flowing through the first coil and the current induced in the structure under inspection may induce a current in the second coils 14 that cross the first coil through which current is flowing. While the current induced in some or all of the second coils may be simultaneously sensed, the processing element of one embodiment directs the sense electronics and, in particular, the multiplexer 28 to sense the current induced in each one of the second coils in turn such that the current induced in the second coils is sensed in a sequential manner while current continues to flow through the respective first coil. See steps 42, 46 and 48. Once the current induced in each of the second coils has been sensed, the processing element may direct the AC source and the associated multiplexer to cease the supply of AC current to the first coil that had been energized and to, instead, supply current to another one of the first coils. See steps 50 and 52. The current induced in each of the second coils is then again sensed. This process may then be repeated until current has been supplied to each of the first coils and the current induced in each of the second coils has been sensed while current is flowing through each of the first coils.

In conjunction with the current sensed in each second coil 14, the processing element 26 also associates the current induced within a respective second coil with a respective sensing element 16. See step 44. The respective sensing element is located at the point at which the first coil 12 to which the AC source 22 is electrically connected crosses the respective second coil in which the induced current is sensed. While the eddy current probe 10 is maintained in the same position relative to the structure under inspection, the processing element may associate a sensed current with each of the respective sensing elements.

The eddy current probe 10 may also include a display 32 that is driven by the processing element 26 for depicting at least one characteristic, such as the electrical conductivity, of the structure under inspection based upon the currents induced in respective ones of the second coils 14 and the relative position of the sensing elements 16 associated therewith. See step 54 of FIG. 4. As mentioned above, the current induced in the second coils is indicative of the complex impedance of that portion of the structure proximate the respective sensing element and, as such, has a reactive component and an inductive reactance component. By comparing the sensed current to a predefined threshold, cracks, corrosion, dents, damage attributable to lightning or fire or the like may be identified as a result of variations between the sensed current and the predefined threshold. While the predefined threshold may be defined in various manners, the predefined threshold may be representative of the anticipated current in the absence of cracks, corrosion, dents or other damage that serves to increase the impedance and therefore decrease the resulting sensed currents. In contrast to a predefined threshold, the current sensed by the eddy current probe at one location may be compared to the current sensed by the eddy current probe at another location upon the structure in order to determine the relative difference in the impedance to which the signals are subjected at the two different locations. This relative difference in impedance can, in turn, be utilized to identify cracks, corrosion, dents or other damage. As such, the processing element can drive the display to graphically represent those portions of the object under inspection that may have a crack, corrosion or the like. For example, the exemplary display depicted in FIGS. 1 and 3 illustrates a hole, such as a fastener hole, having a crack extending rightwardly therefrom.

The eddy current probe 10 advantageously generates the display in real time. As such, the eddy current probe need not include a position encoder or other position determining device to track the position of the eddy current probe relative to a reference location upon the structure under inspection as required by conventional manual eddy current inspection devices. Instead, the technician merely places the eddy current probe upon a portion of the structure and views the display that is generated in real time to identify the crack, corrosion or the like in that portion of the structure. Once current has been supplied to each first coil 12 and the current induced in each second coil 14 has been sensed while current is supplied to each first coil, the technician may move the eddy current probe array 18 across the surface of the structure as desired. See steps 56 and 58 of FIG. 4. The technician may move the eddy current probe in any desired pattern and may follow non-linear or other atypical paths, if desired to track the propagation of a crack, for example. Moreover, the technician can move the eddy current probe array continuously across the surface of the structure so long as the current is applied to the coils in a relatively rapid sequence.

As shown in FIG. 1, the entire eddy current probe 10 may be mounted within a housing that is held by a technician and moved over the structure under inspection. The housing is generally formed of an electrically insulating material and, in some embodiments, a thermally insulating material. For example, the housing may be formed of a plastic material with the components bonded therein, such as with an epoxy. In this embodiment, the eddy current probe may be supplied power by batteries that are also resident within the housing or by a remote power supply connected to the eddy current probe by electrical cables or the like.

Alternatively, the eddy current probe array 18 and, in some embodiments, one or both multiplexers 24, 28, may be disposed within a housing that is held by the technician and moved over the surface of the structure under inspection, while the other components, such as the AC source 22, the processing element 26 and the display 32 are electrically connected to, but remote from the eddy current probe array. In this regard, the AC source, the processing element and the display, for example, may be positioned proximate to the object under inspection and electrically connected to the eddy current probe array via either a wired or wireless connection. In order to reduce the number of wires extending to the eddy current probe array, one or both multiplexers may be disposed within the housing. Alternatively, the multiplexers may be remotely located from the housing such that additional wires must extend to and from the housing.

In embodiments in which the display 32 is remote from the eddy current probe array 18, the display is advantageously located such that the technician can view the display while moving the housing including the eddy current probe array across the surface of the structure under inspection. For example, the display may be a liquid crystal display or the like that may be strapped to the wrist of the technician such that the display may be readily viewed by the technician during the process of inspecting the structure. In this embodiment, the additional components, such as the processing element 26, the AC source 22 and any necessary batteries, may be disposed within a backpack, a fanny pack or the like to facilitate the portability of the eddy current probe 10.

Regardless of the components disposed within the housing, the housing is preferably constructed of a plastic epoxy with a relatively thin wall between the eddy current probe array 18 and the surface of the structure to be inspected such that the spacing between the eddy current probe array and the surface of the structure is small. Alternatively, the housing may be constructed from other non-conducting materials, such as glass or plastic. By encasing the components in a plastic epoxy in one embodiment, the plastic epoxy also serves to glue down the wires which reduces deleterious signal noise.

In addition, the surface of the housing that will be located proximate the surface of the structure under inspection will be finished so as to provide a relatively smooth sliding surface. As such, the housing may be placed in contact with the structure and slid therealong. For the eddy current inspection of structures having slight protrusions, such as counter sunk fasteners that may protrude outwardly beyond the remainder of the surface of the structure by as few thousandths of an inch, the housing may include one or more ski-like protrusions that extend from the surface of the housing proximate the surface of the structure under inspection to facilitate sliding of the housing along the surface of the structure without butting into or otherwise contacting the protruding elements. Additionally, the housing may have beveled edges proximate the surface of the housing that will be in contact with the structure under inspection in order to facilitate the sliding of the housing over structures having relatively rough surfaces.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An eddy current probe for inspecting a structure comprising:
a plurality of first coils oriented in a first direction;
an alternating current source electrically connected to respective ones of the plurality of first coils;
a plurality of second coils oriented in a second direction, different than the first direction, such that the plurality of second coils cross the plurality of first coils to define respective sensing elements, wherein each of the first and second coils is elongated, wherein each first coil defines a first major axis extending in the first direction, wherein each second coil defines a second major axis extending in the second direction, and wherein said first and second coils comprise a plurality of turns of a conductive member; and
sense electronics for sensing current induced in respective ones of the plurality of second coils,
wherein the current sensed in a respective second coil is representative of at least one characteristic of the structure proximate the corresponding sensing element.

2. An eddy current probe according to claim 1 wherein the alternating current source is sequentially connected to each of the first coils, and wherein the sense electronics sequentially senses the current induced in each of the second coils while the alternating current source provides current to a respective first coil.

3. An eddy current probe according to claim 2 further comprising a multiplexer for sequentially connecting the alternating current source to each of the first coils.

4. An eddy current probe according to claim 2 wherein the sense electronics comprises a multiplexer for sequentially connecting to each of the second coils in order to sense the current induced therein.

5. An eddy current probe according to claim 1 wherein the sense electronics comprises a processing element for associating the current induced within a respective second coil with a respective sensing element defined by the first coil to which the alternating current source is electrically connected and the respective second coil.

6. An eddy current probe according to claim 5 further comprising a display, responsive to die processing element, for depicting at least one characteristic of the structure based upon the currents induced in respective ones of the second coils.

7. An eddy current probe according to claim 1 wherein each coil crosses a plurality of other coils to define a plurality of sensing elements.

8. An eddy current probe according to claim 1 wherein the first and second coils are oriented in first and second directions, respectively, that extend perpendicular to one another.

9. An eddy current probe for inspecting a structure comprising:
a plurality of first coils oriented in a first direction;
an alternating current source electrically connected to respective ones of the plurality of first coils;
a plurality of second coils oriented in a second direction, different than the first direction, such that the plurality of second coils cross the plurality of first coils to define respective sensing elements;
sense electronics for sensing current induced in respective ones of the plurality of second coils; and
a plurality of magnetically permeable core elements at least partially encircled by respective pairs of said first and second coils
wherein the current sensed in a respective second coil is representative of at least one characteristic of the structure proximate the corresponding sensing element.

10. An eddy current probe array for inspecting a structure comprising:
a plurality of elongated first coils oriented in a first direction, wherein each first coil defines a first major axis extending in the first direction; and
a plurality of elongated second coils oriented in a second direction, different than the first direction, such that the plurality of second coils cross the plurality of first coils to define respective sensing elements responsive to eddy currents induced in the structure, wherein each second coil defines a second major axis extending in the second direction,
wherein said first and second coils comprise a plurality of turns of a conductive member, and
wherein current sensed in a respective second coil is representative of at least one characteristic of the structure proximate the corresponding sensing element.

11. An eddy current probe array according to claim 10 wherein each coil crosses a plurality of other coils to define a plurality of sensing elements.

12. An eddy current probe array according to claim 10 wherein the first and second coils are oriented in first and second directions, respectively, that extend perpendicular to one another.

13. An eddy current probe array for inspecting a structure comprising:
a plurality of elongated first coils oriented in a first direction;
a plurality of elongated second coils oriented in a second direction, different than the first direction, such that the plurality of second coils cross the plurality of first coils to define respective sensing elements; and
a plurality of magnetically permeable core elements at least partially encircled by respective pairs of said first and second coils,
wherein current sensed in a respective second coil is representative of at least one characteristic of the structure proximate the corresponding sensing element.

14. An eddy current probe array for inspecting a structure comprising:
a plurality of elongated first coils oriented in a first direction;
a plurality of elongated second coils oriented in a second direction, different than the first direction, such that the plurality of second coils cross the plurality of first coils to define respective sensing elements; and
a plurality of magnetically permeable core elements including:
a plurality of medial core elements; and
a plurality of peripheral core elements disposed about the medial core elements
wherein current sensed in a respective second coil is representative of at least one characteristic of the structure proximate the corresponding sensing element.

15. An eddy current probe array according to claim 14 wherein the plurality of core elements are disposed in a two-dimensional array having a plurality of linear arrangements of the core elements, wherein at least one linear arrangement comprises a plurality of medial core elements disposed between a pair of peripheral core elements such that one of the first and second coils is wrapped about the pair of peripheral core elements so as to also encircle the plurality of medial core elements disposed therebetween.

16. A method of conducting an eddy current inspection of a structure, the method comprising;

positioning an eddy current probe array proximate the structure to be inspected, wherein positioning the eddy current probe array comprises providing the eddy current probe array comprising a plurality of elongated first coils oriented in a first direction and defining a first major axis extending in the first direction and a plurality of elongated second coils oriented in a second direction, different than the first direction, such that the plurality of second coils cross the plurality of first coils to define respective sensing elements, wherein each second coil defines a second major axis extending in the second direction, and wherein said first and second coils comprise a plurality of turns of a conductive member;

supplying alternating current to at least one of the plurality of first coils oriented in the first direction; and sensing current induced in at least one of the plurality of second coils that are oriented in the second direction, wherein the current sensed in a respective second coil is representative of at least one characteristic of the structure proximate the corresponding sensing element defined by the crossing of the respective second coil and the first coil to which current is supplied.

17. A method according to claim 16 wherein alternating current is sequentially supplied to each of the first coils, and wherein the current induced in each of the second coils is sequentially sensed while the alternating current is provided to a respective first coil.

18. A method according to claim 17 further comprising moving the plurality of first and second coils relative to the structure under inspection once alternating current has been supplied to each first coil and once the current induced in each second coil has been sensed while current is supplied to each first coil.

19. A method according to claim 16 further comprising associating the current induced within a respective second coil with a respective sensing element defined by the first coil to which the alternating current is supplied and the respective second coil.

20. A method according to claim 19 further comprising displaying the at least one characteristic of the structure under inspection based upon the currents induced in respective ones of the second coils.

* * * * *